(12) United States Patent
Schütze et al.

(10) Patent No.: US 10,697,894 B2
(45) Date of Patent: Jun. 30, 2020

(54) DEVICE AND METHOD FOR CHECKING A MATERIAL FOR TRANSPLANTATION

(71) Applicant: CellTool GmbH, Bernried (DE)

(72) Inventors: Karin Schütze, Tutzing (DE); Raimund Schütze, Tutzing (DE)

(73) Assignee: CellTool GmbH (DE)

( * ) Notice: Subject to any disclaimer, the term of this patent is extended or adjusted under 35 U.S.C. 154(b) by 0 days.

(21) Appl. No.: 15/553,342

(22) PCT Filed: Feb. 24, 2016

(86) PCT No.: PCT/EP2016/053863
§ 371 (c)(1),
(2) Date: Aug. 24, 2017

(87) PCT Pub. No.: WO2016/135194
PCT Pub. Date: Sep. 1, 2016

(65) Prior Publication Data
US 2018/0073984 A1    Mar. 15, 2018

(30) Foreign Application Priority Data
Feb. 27, 2015    (DE) .................. 10 2015 203 537

(51) Int. Cl.
*G01N 21/65*    (2006.01)
*G01J 3/44*    (2006.01)
*G01N 33/483*    (2006.01)

(52) U.S. Cl.
CPC ............... *G01N 21/65* (2013.01); *G01J 3/44* (2013.01); *G01N 33/4833* (2013.01)

(58) Field of Classification Search
CPC ........ G01N 21/65; G01N 33/4833; G01J 3/44
USPC ........................................................ 356/301
See application file for complete search history.

(56) References Cited

U.S. PATENT DOCUMENTS

| 2006/0250613 A1* | 11/2006 | Demuth | G01J 3/32 356/301 |
| 2007/0049831 A1* | 3/2007 | Crowther | G01J 3/44 600/473 |
| 2010/0034743 A1* | 2/2010 | Cohen | G01J 3/02 424/9.1 |
| 2010/0315628 A1 | 12/2010 | Mertsching et al. | |

(Continued)

FOREIGN PATENT DOCUMENTS

| DE | 102006053540 B3 | 1/2008 |
| DE | 102010023099 B3 | 11/2011 |
| WO | 2014129970 A1 | 8/2014 |

OTHER PUBLICATIONS

Pudlas et al. ("Raman spectroscopy as a tool for quality and sterility analysis for tissue engineering applications like cartilage transplants", Int J Artif Organs 2010; 33 (3): 228-237).*

(Continued)

*Primary Examiner* — Hina F Ayub
(74) *Attorney, Agent, or Firm* — The Webb Law Firm

(57) ABSTRACT

In order to check a material for transplantation, at least one Raman spectrum (41, 42) of the material is detected. An electronic evaluation device determines an information, from which depends a suitability of the material for use during the transplantation, by evaluating the at least one Raman spectrum (41, 42).

18 Claims, 10 Drawing Sheets

(56) References Cited

U.S. PATENT DOCUMENTS

| | | | |
|---|---|---|---|
| 2011/0122407 A1* | 5/2011 | Jalali | G01N 21/65 356/301 |
| 2013/0171685 A1 | 7/2013 | Schütze et al. | |
| 2014/0028996 A1* | 1/2014 | Liu | G01J 3/44 356/51 |
| 2016/0061808 A1* | 3/2016 | Cheung | G01N 33/4833 600/476 |
| 2016/0202222 A1* | 7/2016 | Roberts | G01N 1/2202 435/5 |
| 2017/0020460 A1* | 1/2017 | Leblond | A61B 5/0075 |

OTHER PUBLICATIONS

Shevchenko et al. ("A review of tissue-engineered skin bioconstructs available for skin reconstruction", J. R. Soc. Interface (2010) 7, 229-258).*

Biederman et al., "Tissue Engineering of Skin for Wound Coverage", 2013, pp. 375-382, vol. 20, No. 5, Eur J Pediatr Surg.

Celltool, "BioRam—Photonic fingerprinting Raman spectroscopy for living cells" Nov. 2011, pp. 1-9, downloaded from http://celltool.de/files/celltool-bioram-flyer_en.pdf.

Marino et al., "Bioengineering Dermo-Epidermal Skin Grafts with Blood and Lymphatic Capillaries", Jan. 29, 2014, vol. 6, No. 221, www.ScienceTranslation.org, Zurich Switzerland.

Pontiggia et al. Optimizing in vitro culture conditions leads to a significantly shorter production time of human dermo-epidermal skin substitutes, Pediatr Surg Int., 2013, pp. 249-256, vol. 29, Springer, Zurich, Switzerland.

Pudlas et al., "Non-invasive identification of proteoglycans and chondrocyte differentiation state by Raman microspectroscopy", J Biophotonics, 2013, pp. 205-211, vol. 6, No. 2, Wiley-VCH, Weinheim.

Tollefson et al., "Raman spectral imaging of prostate cancer: can Raman molecular imaging be used to augment standard histopathology?", 2010, pp. 484-488, vol. 106, No. 4, BJU International.

Pudlas et al., "Raman Spectroscopy: A Noninvasive Analysis Tool for the Discrimination of Human Skin Cells", Tissue Engineering, 2011, Part C, vol. 17, pp. 1027-1040.

Wikipedia, Histology, HTTPS://en.wikipedia.org/wiki/Histology ( printed from the internet Jul. 10, 2018).

* cited by examiner

DEVICE AND METHOD FOR CHECKING A MATERIAL FOR TRANSPLANTATION

CROSS-REFERENCE TO RELATED APPLICATIONS

This application is the United States national phase of International Application No. PCT/EP2016/053863 filed Feb. 24, 2016, and claims priority to German Patent Application No. 10 2015 203 537.9 filed Feb. 27, 2015, the disclosures of which are hereby incorporated in their entirety by reference.

FIELD OF THE INVENTION

Exemplary embodiments of the invention relate to devices and methods for checking material for transplantation. Exemplary embodiments of the invention relate to, in particular, devices and methods which make it possible to check whether the material is suitable for use as transplant.

BACKGROUND

Transplantations of cultured tissue are used to a large extent. For example, skin wounds or skin disorders may make it necessary to carry out skin transplantation. To this end, it is possible to remove a skin transplant at one body site and to transplant it to another body site. However, such techniques may be unsatisfactory especially when there are relatively extensive skin wounds or skin disorders. Examples of such skin lesions can include burns with skin injuries that are extensive and deep, large birthmarks or chronic wounds.

To avoid such problems, it is possible to use cultured skin in order to treat the skin lesions. Skin cells can be removed in a biopsy and applied to a matrix or embedded in said matrix. In the matrix, the skin cells can grow to form dermis and epidermis. In this way, it is possible to culture so-called skin grafts. Other techniques for carrying out "tissue engineering", by means of which material can be generated for skin transplantation, can be used. Exemplary techniques for generating skin substitutes by "tissue engineering" are, for example, described in T. Biedermann et al., "Tissue engineering of skin for wound coverage." European Journal of Pediatric Surgery, 23(05): 375-382 (2013); L. Pontiggia et al., "Optimizing in vitro culture conditions leads to a significantly shorter production time of human dermo-epidermal skin substitutes". Pediatric Surgery International, 29(3): 249-256 (2013); or D. Marino et al., "Bioengineering dermo-epidermal skin grafts with blood and lymphatic capillaries". Science Translational Medicine, 6(221): 221ra14 (2014).

One challenge in the use of cultured skin or other techniques for producing skin substitutes is checking the material as to whether it is suitable for use in the transplantation. The suitability of the material for use in the skin transplantation depends, for example, on the number of cells and/or on a ratio of the cell number of different cell types. Furthermore, the suitability of the material for use in the skin transplantation can also depend on whether and to what extent cells are functionally impaired, for example by apoptosis or necrosis.

There are similar challenges in the use of other cultured tissues as transplant, such as, for example, cartilage substitute or bone substitute.

To check the material for its suitability for use in the transplantation, it is, for example, possible for a sorting of the fully cultured cell populations by means of flow cytometry before the introduction into the matrix. The so-called "DNA count" method is used in order to count the number of total cells in the fully cultured matrix. However, such techniques are expensive and time-consuming. Depending on the implementation, such techniques may also involve a partial destruction of the material to be tested for its suitability for use as transplant. Furthermore, such techniques also only provide limited information or do not provide any information about the functionality and/or quality of the cells.

Moreover, when carrying out the flow cytometry, it is necessary to culture a large number of cells beforehand in order to allow the measurement. This is time-consuming and cost-intensive (e.g., in the case of fluorescence labeling via antibody-based labels). The cells are no longer available to the patient. The flow cytometry does not provide any information about the final cell count, the ratio of the number of different cell types and/or the quality of the cells in a transplant cultured to completion.

"DNA count" methods can be set up on a portion of the transplant, but do not provide any information about the cell types and/or the ratio of different cell types.

SUMMARY

There is a need for devices and methods for checking material for its suitability as transplant. In particular, there is a need for such devices and methods in which it is possible to objectively determine on the basis of quantitative and/or qualitative measured values as to whether the material exhibits one or more properties which make it suitable for use in transplantation.

The material which is examined using the devices and methods can comprise cells or consist of cells. The material can comprise a support material such as a matrix, for example a collagen matrix. The devices and methods can be configured such that the cells and the support material, for example the matrix, are both separately subjected to a quality control. Alternatively or additionally, the devices and methods can be configured to subject the cells and/or the support material, for example the matrix, in a tissue transplant to a quality control after cultivation of the cells.

According to exemplary embodiments of the invention, a material is examined by carrying out Raman spectroscopy. One or more Raman spectra can be analyzed in order to identify, on the basis of the Raman spectrum or on the basis of multiple Raman spectra, whether the material is suitable for use in transplantation. For example, one or more Raman spectra can be analyzed in order to determine a number of cells of a particular cell type in the material and/or a ratio of the number of cells of different cell types.

The evaluation of one or more Raman spectra makes it possible to examine the material objectively and quantitatively. It is possible to perform a comparison with reference spectra stored in a database in order to determine which cell types are present and in order to quantify the number of cells of one or more cell types. Alternatively or additionally, it is possible to process the Raman spectra, for example by means of a cluster analysis, in order to identify different cell types.

One exemplary embodiment specifies a device for checking a material for transplantation. The device comprises a Raman spectroscopy system for carrying out Raman spectroscopy on the material in order to record at least one Raman spectrum. The device comprises an electronic evaluation unit configured to determine, depending on an evaluation of the at least one Raman spectrum, an item of information on which a suitability of the material for use in the transplantation depends.

The material can be a material for an autologous transplantation or an allogeneic transplantation.

The material can be an autologous skin substitute or an allogeneic skin substitute. The material can be an autologous cartilage substitute or an allogeneic cartilage substitute. The material can be an autologous bone substitute or an allogeneic bone substitute.

The material can comprise a skin transplant. The material can comprise artificial skin. The material can comprise cultured cartilage tissue. The material can comprise cultured bone tissue.

The material can comprise cells. The device can be configured to subject the cells to Raman spectroscopy before application to or introduction into a support material, for example a matrix. The device can be configured to automatically determine whether the cells are suitable for introduction into a support material, for example a matrix. The device can be configured to automatically determine which cell types are present and/or in what quantitative proportions different cell types are present. The device can be configured to record contaminations and/or functional impairments of the cells in a qualitative or quantitative manner from the at least one Raman spectrum.

Alternatively or additionally, the device can be configured to subject the cells to Raman spectroscopy after application to or introduction into a support material, for example a matrix. The device can be configured to automatically determine whether the cells in the transplant comprising the cells are suitable for the transplantation. The device can be configured to automatically determine which cell types are present and/or in what quantitative proportions different cell types are present. The device can be configured to record contaminations and/or functional impairments of the cells in the support material, for example the matrix, in a qualitative or quantitative manner from the at least one Raman spectrum.

The material can comprise a support material, for example a matrix, into which the cells are introduced or to which the cells are applied. The matrix can consist of collagen or a different material. The device can be configured to subject the support material, for example the matrix, to Raman spectroscopy before application of the cells to a matrix or introduction of the cells into a matrix. The device can be configured to automatically determine whether the support material, for example the matrix, is suitable for the introduction of the cells. The device can be configured to automatically determine whether the support material, for example the matrix, consists of the desired material. The device can be configured to record contaminations of the support material, for example the matrix, in a qualitative or quantitative manner from the at least one Raman spectrum. The contaminations can be pathogens, bacteria or other foreign bodies. The contaminations can be contaminations of the cell population which should be present in the cultured tissue.

Alternatively or additionally, the device can be configured to subject the support material, for example the matrix, to Raman spectroscopy after the application or introduction of the cells. The device can be configured to automatically determine whether the support material, for example the matrix, in the transplant comprising the matrix is suitable for the transplantation. The device can be configured to record contaminations and/or functional impairments of the matrix in a qualitative or quantitative manner from the at least one Raman spectrum.

The item of information on which the suitability of the material for use in the transplantation depends can comprise a number of cells of a particular cell type per volume or per area. The item of information can comprise the number of keratinocytes per volume or per area. Alternatively or additionally, the item of information can comprise the number of melanocytes per volume or per area. Alternatively or additionally, the item of information can comprise the number of fibroblasts per volume or per area. The item of information can quantitatively or qualitatively indicate whether contaminations of the cell population by foreign cells are present and, if present, which ones.

Alternatively or additionally, the item of information can comprise the number of blood-vessel cells per volume or per area. Alternatively or additionally, the item of information can comprise the number of hair-follicle cells per volume or per area. Alternatively or additionally, the item of information can the functionality of hair-follicle cells. Alternatively or additionally, the item of information can comprise the number of corneocytes per volume or per area.

Alternatively or additionally, the item of information can comprise the number of sebaceous-gland cells per volume or per area. Alternatively or additionally, the item of information can comprise the number of sweat-gland cells per volume or per area.

The electronic evaluation unit can be configured to identify, by means of the evaluation of the at least one Raman spectrum, at least one cell population of the material, which population is selected from the group consisting of: keratinocytes, melanocytes, fibroblasts, blood-vessel cells, hair-follicle cells, corneocytes, sebaceous-gland cells and sweat-gland cells in skin transplants.

The electronic evaluation unit can be configured to identify, by means of the evaluation of the at least one Raman spectrum, at least two different cell populations of the material, of which each is selected from the group consisting of: keratinocytes, melanocytes, fibroblasts, blood-vessel cells, hair-follicle cells, corneocytes, sebaceous-gland cells and sweat-gland cells in skin transplants.

The electronic evaluation unit can be configured to identify, by means of the evaluation of the at least one Raman spectrum, at least two different cell populations of the material, of which each is selected from the group consisting of: chondrocytes, chondroclasts and chondroblasts in cartilage transplants.

The electronic evaluation unit can be configured to identify, by means of the evaluation of the at least one Raman spectrum, at least two different cell populations of the material, of which each is selected from the group consisting of: osteocytes, osteoclasts and osteoblasts in bone transplants.

The electronic evaluation unit can be configured to identify, by means of the evaluation of the at least one Raman spectrum, at least two different cell populations of the material, of which each is selected from the group consisting of: keratinocytes, melanocytes and fibroblasts.

The electronic evaluation unit can be configured to identify, by means of the evaluation of the at least one Raman spectrum, at least two different cell populations of the material, of which each is selected from the group consisting of: chondrocytes, chondroclasts and chondroblasts.

The electronic evaluation unit can be configured to identify, by means of the evaluation of the at least one Raman spectrum, at least two different cell populations of the material, of which each is selected from the group consisting of: osteocytes, osteoclasts and osteoblasts.

The electronic evaluation unit can be configured to determine a composition of the material in at least one region of the material. The electronic evaluation unit can be configured to identify, by means of the evaluation of the at least one Raman spectrum for at least one region of the material, which cell types are present. The electronic evaluation unit can be configured to identify, by means of the evaluation of the at least one Raman spectrum for at least one region of the material, in what quantitative ratio different cell types are present. The different cell types can be keratinocytes, melanocytes and fibroblasts.

The Raman spectroscopy system can be configured to evaluate multiple Raman spectra in order to carry out a cluster analysis, by means of which relative proportions of different cell types are identified.

The Raman spectroscopy system can be configured to record multiple Raman spectra in multiple depths of the material. The electronic evaluation unit can be configured to determine the composition of the material for each of the multiple depths from the respectively recorded Raman spectra.

The electronic evaluation unit can be configured to carry out a cluster analysis of the at least one Raman spectrum. The electronic evaluation unit can be configured to carry out a principal component analysis of the at least one Raman spectrum in order to distinguish different cell types.

The electronic evaluation unit can be configured to determine, depending on the cluster analysis, what proportion of keratinocytes, melanocytes, fibroblasts and/or endothelial cells is present in at least one region of the material.

The electronic evaluation unit can comprise a memory which stores information about the position of Raman peaks of different cell types of an autologous dermo-epidermal skin substitute.

Alternatively or additionally, the electronic evaluation unit can be configured to use a machine-learning method, especially a supervised-learning method, in order to learn an assignment of Raman spectra and cell types. The cell types can encompass keratinocytes, melanocytes, fibroblasts and/or endothelial cells. The cell types can encompass keratinocytes, melanocytes, fibroblasts, blood-vessel cells, hair-follicle cells, corneocytes, sebaceous-gland cells and sweat-gland cells.

The cell types can encompass chondrocytes, chondroclasts and chondroblasts.

The cell types can encompass osteocytes, osteoclasts and osteoblasts.

The electronic evaluation unit can be configured to determine, depending on the evaluation of the at least one Raman spectrum, a total number of cells in the material. To this end, a spectral weight of at least one Raman peak can be ascertained. Alternatively or additionally, it is possible to determine a number or a weight of data points which are ascertained with a principal component analysis or a different cluster analysis of the at least one Raman spectrum in order to determine the total number of cells of a cell type or of multiple different cell types in the material.

The electronic evaluation unit can be configured to identify, depending on the evaluation of the at least one Raman spectrum, functional changes, especially an apoptosis and/or necrosis, of at least one cell population of the material.

The electronic evaluation unit can be configured to output an item of information as to whether the cultured tissue is suitable for transplantation, after the evaluation of multiple Raman spectra has been carried out, which evaluation was used to assess the support material of a cultured tissue and/or the cells of the cultured tissue. Said item of information can be an item of binary information which, in the manner of a "Yes or No" statement, defines whether the cultured tissue is usable as transplant.

The material can comprise a skin transplant. The material can comprise artificial skin. The artificial skin can be cultured skin. The artificial skin can be in particular an autologous dermo-epidermal skin substitute.

The artificial skin can comprise a support material, especially a biodegradable support material, and autologous cellular material.

A method for checking a material for transplantation comprises recording at least one Raman spectrum of the material and determining, by means of evaluation of the at least one Raman spectrum, an item of information on which a suitability of the material for use in the transplantation depends.

The method can be carried out by the device according to one exemplary embodiment.

The determination of the item of information on which the suitability of the material for use in the transplantation depends can be done automatically by means of an electronic calculation unit.

The material checked in the method can be a material for an autologous transplantation.

In the method, the material can comprise cells. The method can comprise evaluating the at least one Raman spectrum before the introduction of the cells into a support material, for example a matrix, and/or after the introduction into the support material, for example the matrix, as has been described in connection with the device.

In the method, the material can comprise a support material, for example a matrix. The method can comprise evaluating the at least one Raman spectrum of the support material, for example the matrix, before the cells are introduced and/or after the introduction into the support material, for example the matrix, as has been described in connection with the device.

The material checked in the method can be an autologous dermo-epidermal skin substitute.

In the method, the item of information on which the suitability of the material for use in the transplantation depends can comprise a number of cells of a particular cell type per volume or per area. In the method, the item of information can comprise the number of keratinocytes per volume or per area. Alternatively or additionally, in the method, the item of information can comprise the number of melanocytes per volume or per area. Alternatively or additionally, in the method, the item of information can comprise the number of fibroblasts per volume or per area.

Alternatively or additionally, in the method, the item of information can comprise the number of blood-vessel cells per volume or per area. Alternatively or additionally, in the method, the item of information can comprise the number of hair-follicle cells per volume or per area. Alternatively or additionally, in the method, the item of information can comprise the number of hair-follicle cells per volume or per area.

Alternatively or additionally, in the method, the item of information can comprise the number of hair-follicle cells per volume or per area. Alternatively or additionally, in the method, the item of information can comprise the number of corneocytes per volume or per area. Alternatively or additionally, in the method, the item of information can comprise the number of sebaceous-gland cells per volume or per area.

Alternatively or additionally, in the method, the item of information can comprise the number of sweat-gland cells per volume or per area.

In the method, it is possible to identify, by means of the evaluation of the at least one Raman spectrum, at least one cell population of the material, which population is selected from the group consisting of: keratinocytes, melanocytes, fibroblasts, blood-vessel cells, hair-follicle cells, corneocytes, sebaceous-gland cells and sweat-gland cells.

In the method, it is possible to identify, by means of the evaluation of the at least one Raman spectrum, at least two different cell populations of the material, of which each is selected from the group consisting of: keratinocytes, melanocytes, fibroblasts, blood-vessel cells, hair-follicle cells, corneocytes, sebaceous-gland cells and sweat-gland cells.

In the method, it is possible to identify, by means of the evaluation of the at least one Raman spectrum, at least two different cell populations of the material, of which each is selected from the group consisting of: keratinocytes, melanocytes and fibroblasts.

In the method, it is possible to identify, by means of the evaluation of the at least one Raman spectrum, at least two different cell populations of the material, of which each is selected from the group consisting of: chondrocytes, chondroclasts and chondroblasts.

In the method, it is possible to identify, by means of the evaluation of the at least one Raman spectrum, at least two different cell populations of the material, of which each is selected from the group consisting of: osteocytes, osteoclasts and osteoblasts.

In the method, the electronic evaluation unit can determine a composition of the material in at least one region of the material from the at least one Raman spectrum. To this end, it is possible to identify, by means of the evaluation of the at least one Raman spectrum for at least one region of the material, which cell types are present. It is possible to identify, by means of the evaluation of the at least one Raman spectrum for at least one region of the material, in what quantitative ratio different cell types are present. The different cell types can be keratinocytes, melanocytes and fibroblasts.

In the method, it is possible to record multiple Raman spectra in multiple depths of the material. The composition of the material can be determined for each of the multiple depths from the respectively recorded Raman spectra.

In the method, the evaluation of the at least one Raman spectrum can comprise carrying out a cluster analysis of the at least one Raman spectrum. In the method, the evaluation of the at least one Raman spectrum can comprise carrying out a principal component analysis of the at least one Raman spectrum in order to distinguish different cell types.

In the method, it is possible to determine, depending on the cluster analysis, what proportion of keratinocytes, melanocytes, fibroblasts and/or endothelial cells is present in at least one region of the material.

In the method, it is possible to determine, depending on the cluster analysis, what proportion of chondrocytes, chondroclasts, chondroblasts is present in at least one region of the material.

Alternatively or additionally, in the method, it is possible to determine, depending on the cluster analysis, what proportion of osteocytes, osteoclasts or osteoblasts is present in at least one region of the material.

In the method, the evaluation of the at least one Raman spectrum can comprise a comparison with information stored in a memory about the position of Raman peaks of different cell types of an autologous dermo-epidermal skin substitute.

In the method, the evaluation of the at least one Raman spectrum can comprise a comparison with information stored in a memory about the position of Raman peaks of different cell types of an autologous cartilage substitute and/or bone substitute.

Alternatively or additionally, the method can comprise carrying out a machine-learning method, especially a supervised-learning method, by means of the electronic evaluation unit in order to learn an assignment of Raman spectra and cell types. The cell types can comprise keratinocytes, melanocytes, fibroblasts and/or endothelial cells. The cell types can comprise keratinocytes, melanocytes, fibroblasts, blood-vessel cells, hair-follicle cells, corneocytes, sebaceous-gland cells and sweat-gland cells.

In the method, the electronic evaluation unit can determine, depending on the evaluation of the at least one Raman spectrum, a total number of cells in the material. To this end, a spectral weight of at least one Raman peak can be ascertained. Alternatively or additionally, in the method, it is possible to determine a number or a weight of data points which are ascertained with a principal component analysis or a different cluster analysis of the at least one Raman spectrum in order to determine the total number of cells of a cell type or of multiple different cell types in the material.

The method can comprise identifying, depending on the evaluation of the at least one Raman spectrum, functional changes, especially an apoptosis and/or necrosis, of at least one cell population of the material.

The material checked in the method can comprise a transplant. The transplant can comprise cultured tissue, for example cultured skin, cultured cartilage or cultured bone tissue.

The material checked in the method can comprise artificial skin. The artificial skin can be cultured skin. The artificial skin can be in particular an autologous dermo-epidermal skin substitute.

The artificial skin can comprise a support material, especially a biodegradable support material, and autologous cellular material.

The methods according to exemplary embodiments can be carried out away from the human or animal body. The device according to exemplary embodiments can be used for an examination of the material, the examination being carried out away from the human or animal body.

The method can comprise generating the material, involving introducing autologous skin cells onto or into a support material, especially a biodegradable matrix.

The methods according to exemplary embodiments can be designed such that obtaining the autologous skin material is not part of the claimed methods.

Devices and methods according to exemplary embodiments allow a rapid, label-free and nondestructive checking of an autologous dermo-epidermal skin substitute or of a different material with respect to its suitability for use in transplantation.

BRIEF DESCRIPTION OF THE FIGURES

The invention will be more particularly elucidated below on the basis of preferred exemplary embodiments with reference to the drawing.

DESCRIPTION OF EXEMPLARY EMBODIMENTS

Exemplary embodiments are described with reference to the figures, in which similar reference signs refer to similar features. The features of the different embodiments described can be combined with one another, if this is not expressly excluded in the following description.

Devices and methods according to exemplary embodiments can be used to examine a material in order to determine whether the material is suitable for use in transplantation. Devices and methods according to exemplary embodiments can be used for the automatic checking of an autologous cultured transplant.

While devices and methods are described below in the context of techniques for checking material for use as skin transplant, the exemplary embodiments are not restricted thereto. Devices and methods according to exemplary embodiments can be generally used for checking different types of cultured tissue for its suitability for use as transplant. Further examples of such tissue encompass cartilage tissue or bone tissue.

In the case of devices and methods according to exemplary embodiments, at least one Raman spectrum of a material is recorded. The material can, for example, be cultured skin. The material can be an autologous dermo-epidermal skin substitute, especially an autologous dermo-epidermal skin graft. The material can comprise a support material, for example a biodegradable matrix, and autologous skin cells. The at least one Raman spectrum is evaluated in order to obtain an item of information on which the suitability of the material for use in skin transplantation depends. The item of information can comprise the number of cells of one or more cell types and/or quotients of the number of multiple cell types.

Figure 1:
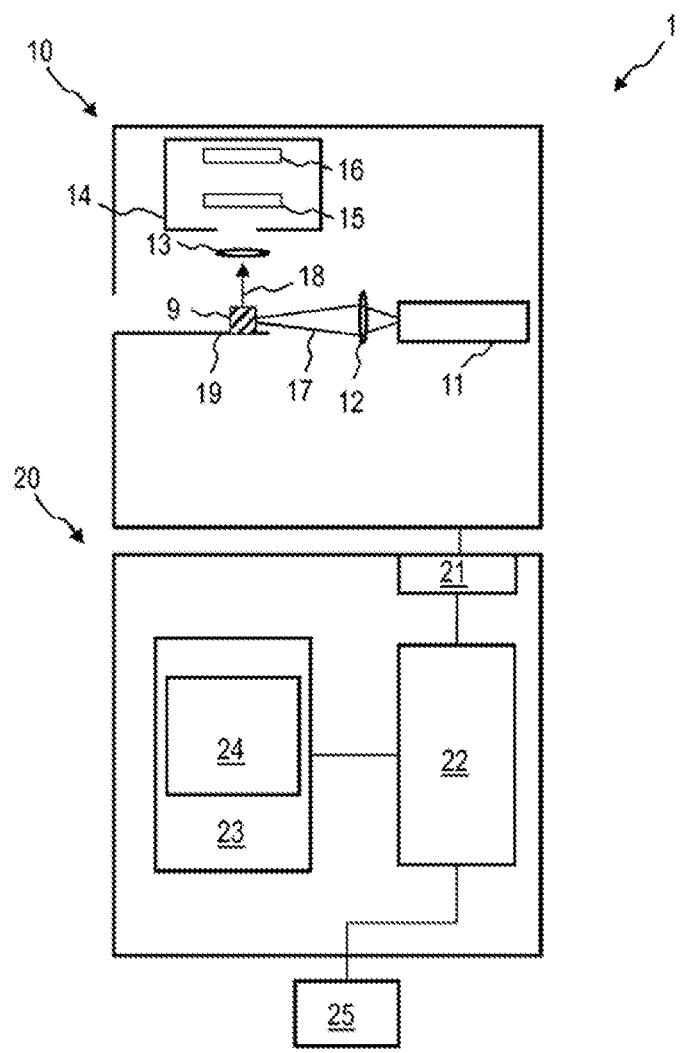
FIG. 1 shows a schematic representation of a device according to one exemplary embodiment.

FIG. 1 is a schematic representation of a device 1 according to one exemplary embodiment. The device 1 is configured to examine a material 9 using Raman spectroscopy and to ascertain, on the basis of one or more recorded Raman spectra, an item of information on which the suitability of the material 9 for use in skin transplantation depends. The relevant checking of the material 9 is done on the basis of at least one Raman spectrum, which the device 1 records and can automatically evaluate. The material 9 can be mounted on a support 19 in order to record the at least one Raman spectrum.

The device 1 comprises a Raman spectroscopy system 10 and an evaluation unit 20. The Raman spectroscopy system 10 is configured to record a Raman spectrum of the material 9. The material 9 can be an autologous dermo-epidermal skin substitute, especially an autologous dermo-epidermal skin graft. Obtaining the autologous skin cells is not subject matter of the methods according to exemplary embodiments.

The Raman spectroscopy system 10 comprises a light source 11. The light source 11 can be a laser. The laser can exhibit a laser wavelength gentle to cells. The laser wavelength can be 785 nm. The light source 11 is configured to emit an excitation beam 17. A Raman spectrometer 14 receives light 18 scattered on of the material 9 by Stokes processes and/or anti-Stokes processes. The Raman spectrometer 14 can comprise a diffractive element 15 and an image sensor 16 for recording the Raman spectrum of the material 9. The Raman spectroscopy system 10 can comprise, in a manner known per se, further elements, for example focusing optical elements 12, 13, which can be designed as lenses, and/or diaphragms.

The device 1 comprises an evaluation unit 20. The evaluation unit 20 can be a computer or can comprise a computer. The evaluation unit 20 is coupled to the Raman spectroscopy system 10. The evaluation unit 20 can control the recording of the Raman spectrum by the Raman spectroscopy system 10. The evaluation unit 20 can control the Raman spectroscopy system 10 such that Raman spectra are recorded in a spatially resolved manner at multiple sites of the material 9.

The evaluation unit 20 comprises an interface 21 for receiving data from the image sensor 16 of the Raman spectroscopy system 10. The evaluation unit comprises a semiconductor integrated circuit 22, which can comprise a processor or controller and which is configured to evaluate the recorded Raman spectrum. The semiconductor integrated circuit 22 is configured to ascertain, on the basis of the at least one Raman spectrum, an item of information which has an influence on whether the material 9 is already or still suitable for use in the skin transplantation.

The evaluation unit 20 can output an item of information as to whether the cultured tissue is suitable for transplantation, after an evaluation of multiple Raman spectra has been carried out, which evaluation was used to assess the support material of a cultured tissue and/or the cells of the cultured tissue. Said item of information can be a binary item of information which defines, in the manner of a "Yes or No" statement, whether the cultured tissue is usable as transplant.

As will be described in more detail with reference to FIG. 2 to FIG. 13, the semiconductor integrated circuit 22 can be configured to identify the presence or absence of particular Raman peaks or to determine the spectral weight of Raman peaks, which are associated with different cell types of the autologous dermo-epidermal skin substitute. The semiconductor integrated circuit 22 can, for example, be configured to quantitatively ascertain, by means of evaluation of the at least one Raman spectrum, whether and in what number in a volume of the material 9 keratinocytes, melanocytes, fibroblasts and/or endothelial cells are present.

The material 9 can also comprise blood vessels and/or lymph vessels. The semiconductor integrated circuit 22 can be configured to quantitatively ascertain, by means of evaluation of the at least one Raman spectrum, whether and in what number in a volume of the material 9 blood-vessel cells, hair-follicle cells, corneocytes, sebaceous-gland cells and/or sweat-gland cells are present.

The semiconductor integrated circuit 22 can be configured to determine for the material 9 local changes in Raman signals, which are assigned to different cell populations. In this way, it is possible to determine the composition of the material 9 in a spatially resolved manner. The spatially resolved determination of the composition can be done in a nondestructive manner.

The semiconductor integrated circuit 22 can identify different cell types, for example keratinocytes, melanocytes, fibroblasts and/or endothelial cells, on the basis of the position of Raman peaks for the corresponding cells. Information about the position and/or the spectral weight of different Raman peaks for the different cell types of an autologous demo-epidermal skin substitute can be nonvolatilely stored in a memory of the device 1. Alternatively or additionally, the information about the position and/or the spectral weight of different Raman peaks for the different cell types of an autologous dermo-epidermal skin substitute can be ascertained by the device 1 by supervised-learning methods or other machine-learning techniques.

The semiconductor integrated circuit 22 can process recorded Raman spectra in different ways. For example, it is possible to use statistical methods, for example a principal component analysis or other cluster analysis techniques. Additionally or alternatively, Raman spectra can be compared with reference data in order to determine which cell types are present and in order to determine ratios of different cell types.

The evaluation unit 20 can comprise a memory 23 in which the reference data 24 are stored, which data can be concomitantly used by the semiconductor integrated circuit 22 in the evaluation of the Raman spectrum.

The evaluation unit 20 can comprise an optical and/or acoustic output unit 25 which, depending on the analysis of the at least one Raman spectrum, outputs information indicating whether the material 9 is suitable for use in the skin transplantation. It is possible to output information about the total number of cells of at least one cell type and/or about ratios of the number of cells of different cell types.

Although the evaluation unit 20 and the Raman spectroscopy system 10 are depicted schematically in FIG. 1 as separate units, the functions of the evaluation unit 20 can also be integrated in a housing of the Raman spectroscopy system 10. The Raman spectroscopy system 10 and the evaluation unit 20 can be designed as mobile units, especially as portable units.

Figure 2:
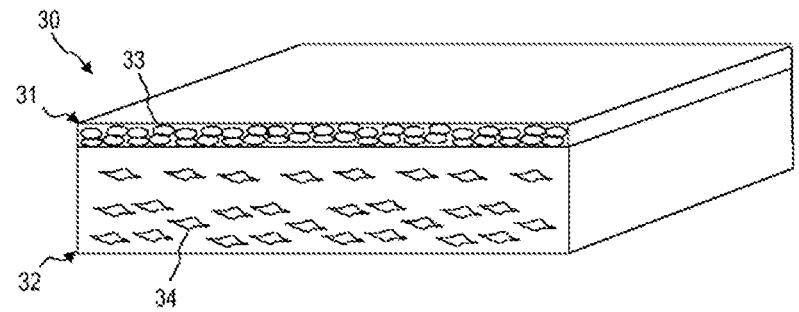
FIG. 2 shows a material which is an autologous demo-epidermal skin substitute, which material can be checked using devices and methods according to exemplary embodiments.

FIG. 2 shows schematically a material 9 which can be examined using devices and methods according to exemplary embodiments. The material 9 can be artificially cultured skin. The material 9 can be generated by removing skin cells and introducing them into or applying them to a matrix or a different support material. The matrix can comprise a hydrogel. The matrix can comprise type 1 collagen. The autologous skin cells can be multiplied. For example, the biopsy can be broken up into the individual cell types, said cell types can be multiplied and then put together again with the aid of an extracellular scaffold. Optionally, pigment cells, blood vessels and/or lymph vessels can be inserted into the material 9. The material 9 can be, though need not be, an autologous dermo-epidermal skin substitute.

The material 9 can comprise an epidermis 31 and a dermis 32. The epidermis 31 can comprise keratinocytes 33. The epidermis can comprise melanocytes. The dermis 32 can comprise fibroblasts 34. It should be understood that, depending on the design of the material 9, the fibroblasts and/or various other constituents of the material 9 can be embedded in hydrogel or a different matrix.

Figure 3:
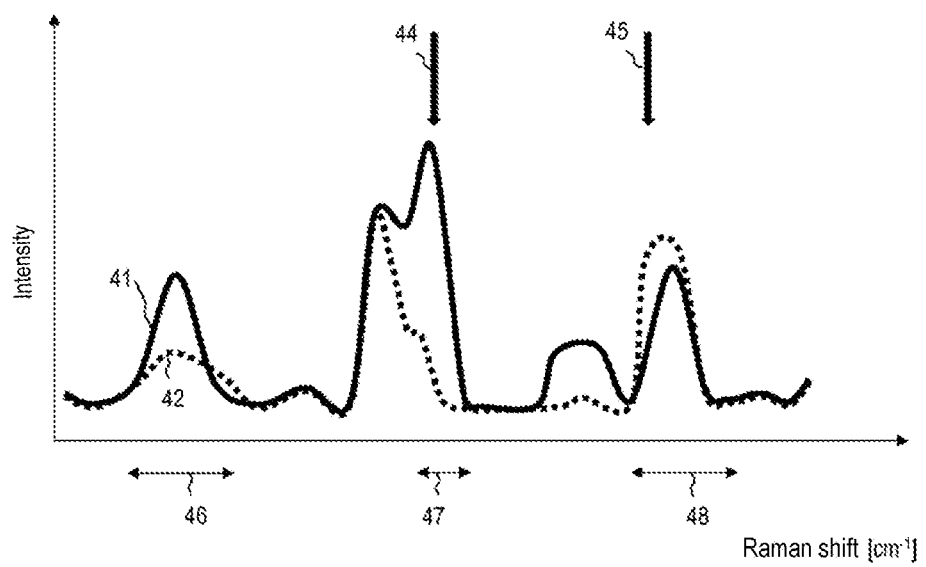
FIG. 3 shows exemplary Raman spectra which are evaluated by a device according to one exemplary embodiment.

FIG. 3 shows Raman spectra for cells of different cell types of a material 9 which is an autologous dermo-epidermal skin substitute. What is depicted by way of example is a portion of a Raman spectrum 41 of keratinocytes and of a Raman spectrum 42 of fibroblasts.

The Raman spectrum 41 of the keratinocytes and the Raman spectrum 42 of the fibroblasts differ in the position and/or the spectral weight of different Raman peaks. These differences can be used by the device 1 for the automatic distinguishing of keratinocytes and fibroblasts.

Different wavenumbers or wavenumber intervals can be evaluated in order to distinguish keratinocytes and fibroblasts. For example, the Raman spectrum 41 of the keratinocytes has a Raman peak 44 at a wavenumber in a wavenumber interval 47 of from 1400 $cm^{-1}$ to 1500 $cm^{-1}$. An analysis of the Raman spectrum in the wavenumber interval 47 makes it possible to distinguish keratinocytes and fibroblasts. Alternatively or additionally, other wavenumber intervals 46, 48 can be evaluated. For example, the intensity of the Raman signal for keratinocytes and fibroblasts differs in a wavenumber interval 46 of from 1600 $cm^{-1}$ to 1670 $cm^{-1}$. In a wavenumber interval 48 of from 1100 $cm^{-1}$ to 1390 $cm^{-1}$, there is a difference in the intensity of the Raman signal for keratinocytes and fibroblasts.

It is not only the position and intensity of Raman peaks 44, 45 of a Raman spectrum which can be evaluated in order to distinguish keratinocytes and fibroblasts.

It is not necessary to compare the Raman spectrum recorded on the material 9 or multiple Raman spectra recorded on the material 9 with information about reference spectra of keratinocytes, melanocytes, fibroblasts and/or endothelial cells. The Raman spectrum or the Raman spectra can be further processed by the evaluation unit 22 in order to distinguish different cell types. The evaluation unit 20 can, for example, carry out a cluster analysis, for example a principal component analysis of the recorded Raman spectra. The result of the cluster analysis can be used in order to distinguish keratinocytes, melanocytes, fibroblasts and/or other cells of the material 9.

The result of the cluster analysis can be used in order to determine quantitative proportions of keratinocytes, melanocytes, fibroblasts and/or other cells of the material 9.

To distinguish different cell types, the Raman spectrum of each cell on which the measurement is carried out can generally comprise a number N of intensities at different wavelengths. The number N can be greater than one, especially much greater than one. By means of a hierarchical clustering, for example in an N-dimensional space, it is possible to take advantage of the fact that, in said space, biochemically similar cells are closer together than biochemically distant cells. By means of the hierarchical clustering, cells which are close together and thus form a cluster can be distinguished from cells which are further removed from one another. On the basis of their position in the data space, the cells are sorted into natural groups or clusters.

In this way, it is possible to identify a plurality of classes or clusters. By means of the comparison of the spectra in each class with the spectra of already identified cells, for example from a pure culture of melanocytes or other relevant cells, it is possible to assign a cell type to each class. The number of cells in each class can be used for the quantitative determination of the proportions. The number of cells in each class divided by the total number of measured spectra can then quantitatively indicate the proportion of the particular cell type in the material.

Figure 4:
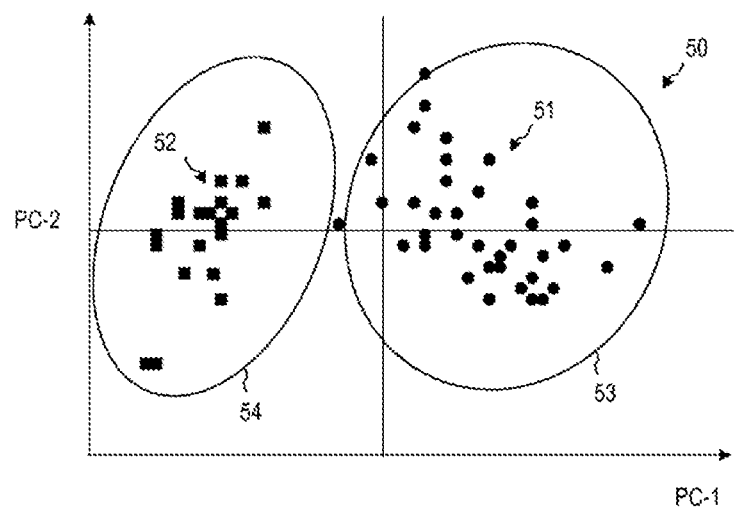
FIG. 4 illustrates processing of recorded Raman spectra by a device according to one exemplary embodiment.

FIG. 4 illustrates exemplary results of a cluster analysis carried out by the evaluation unit 20 in order to determine which cell types are present in a region of the material 9. What is carried out is the principal component analysis for a Raman spectrum or multiple Raman spectra which were recorded on the material 9. The data points are depicted in accordance with a pair of the different principal components PC-1 and PC-2. FIG. 4 shows the data points 51, which are assigned to keratinocytes, and data points 52, which are assigned to fibroblasts.

The result of the cluster analysis of the Raman spectrum recorded on the material 9 can be evaluated as to whether and how many data points lie in different regions 53, 54 of the coordinate system spanned by multiple principal components. For example, it is possible to ascertain how many data points lie in a region 53 assigned to keratinocytes. It is possible to ascertain how many data points lie in a region 54 assigned to keratinocytes. It is possible to ascertain how many data points lie in further regions of the coordinate system spanned by multiple principal components, which regions are assigned to melanocytes or other cellular constituents of the material 9.

As is discernible from FIG. 4, the data points obtained by the principal component analysis shift depending on which cell types are present and how great the proportion of keratinocytes, fibroblasts or other constituents such as melanocytes is in each case. Accordingly, the evaluation unit 20 can, on the basis of the principal component analysis of a Raman spectrum or multiple Raman spectra, automatically determine which cell types are present and/or what proportion of the cells belong to the different cell types.

Figure 5:
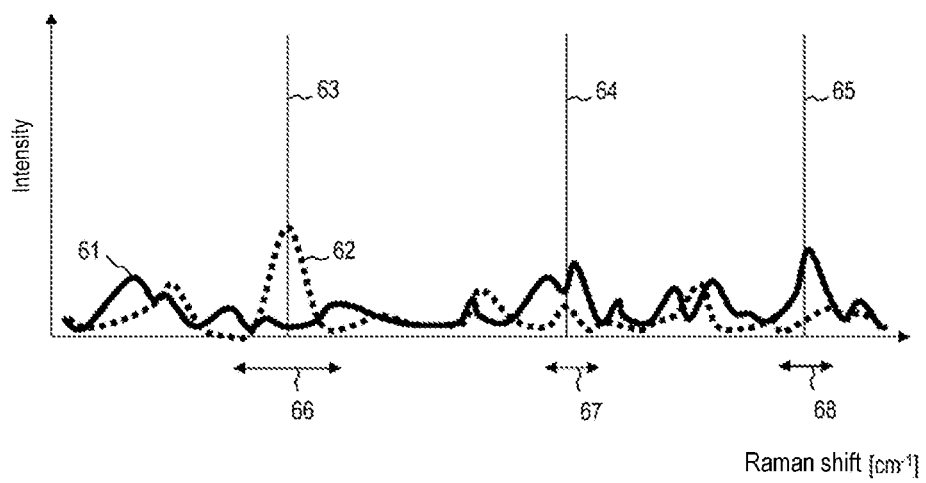
FIG. 5 shows exemplary Raman spectra which are evaluated by a device according to one exemplary embodiment.

FIG. 5 shows Raman spectra for cells of different cell types of a material 9 which is an autologous dermo-epidermal skin substitute. What is depicted by way of example is a portion of a Raman spectrum 61 of melanocytes and of a Raman spectrum 62 of fibroblasts.

The Raman spectrum 61 of the melanocytes and the Raman spectrum 62 of the fibroblasts differ in the position and/or the spectral weight of different Raman peaks. These differences can be used by the device 1 for the automatic distinguishing of melanocytes and fibroblasts.

Different wavenumbers or wavenumber intervals can be evaluated in order to distinguish melanocytes and fibroblasts. For example, the Raman spectrum 62 of the fibroblasts has a Raman peak at a wavenumber 63 in a wavenumber interval 66 of from 1000 cm$^{-1}$ to 1150 cm$^{-1}$. An analysis of the Raman spectrum in the wavenumber interval 66 makes it possible to distinguish melanocytes and fibroblasts. Alternatively or additionally, other wavenumber intervals 67, 68 can be evaluated in order to distinguish melanocytes and fibroblasts on the basis of Raman peaks at different wavenumbers 64, 65. For example, the intensity of the Raman signal for melanocytes and fibroblasts differs in a wavenumber interval 67 of from 1450 cm$^{-1}$ to 1550 cm$^{-1}$. In a wavenumber interval 68 of from 1575 cm$^{-1}$ to 1640 cm$^{-1}$, there is a difference in the intensity of the Raman signal for melanocytes and fibroblasts.

It is not only the position and intensity of Raman peaks of a Raman spectrum which can be evaluated in order to distinguish melanocytes and fibroblasts. The device 1 can use the ratio of the intensities measured at two different Raman peaks in order to infer the proportion of melanocytes and fibroblasts.

A multiplicity of other wavenumber intervals can be used to distinguish keratinocytes, melanocytes, fibroblasts and/or other cells of the material 9.

Figure 6:
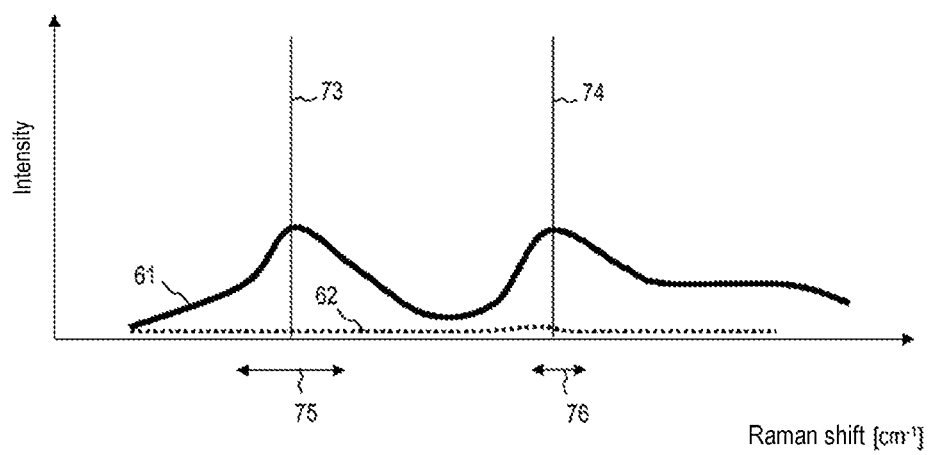
FIG. 6 shows exemplary Raman spectra which are evaluated by a device according to one exemplary embodiment.

FIG. 6 shows Raman spectra for cells of different cell types of a material 9 which is an autologous dermo-epidermal skin substitute. What is depicted by way of example is a portion of a Raman spectrum 61 of melanocytes and of a Raman spectrum 62 of fibroblasts.

The Raman spectrum 61 of the melanocytes has Raman peaks at wavenumbers 73, 74 in a wavenumber interval of from 2350 cm$^{-1}$ to 2650 cm$^{-1}$, whereas the Raman spectrum 62 of the fibroblasts does not have significant Raman peaks there. For example, the Raman spectrum 61 of the melanocytes can have Raman peaks a Raman peak at a wavenumber 73 in a wavenumber interval 75 of from 2400 cm$^{-1}$ to 2450 cm$^{-1}$. The Raman spectrum 61 of the melanocytes can have a Raman peak at a wavenumber 74 in a wavenumber interval 76 of from 2500 cm$^{-1}$ to 2560 cm$^{-1}$.

As already elucidated, it is possible, though not absolutely necessary, to compare the Raman spectrum recorded on the material 9 or multiple Raman spectra recorded on the material 9 with information about reference spectra of keratinocytes, melanocytes, fibroblasts and/or endothelial cells. The Raman spectrum or the Raman spectra can be further processed by the evaluation unit 22 in order to distinguish different cell types. The evaluation unit 20 can, for example, carry out a cluster analysis, for example a principal component analysis of the recorded Raman spectrum. The result of the cluster analysis can be used in order to distinguish keratinocytes, melanocytes, fibroblasts and/or other cells of the material 9.

The recording of Raman spectra can be done on the material 9 in a spatially resolved manner. In this connection, the recording can be done at multiple positions arranged on a surface of the material 9, for example on the epidermis layer. Alternatively or additionally, the Raman spectroscopy also makes it possible to record in different depths of the material 9 without having to destroy the material 9 for this purpose. The points at which a Raman spectrum or multiple Raman spectra is/are recorded in each case can define a regular or irregular lattice.

Figure 7:
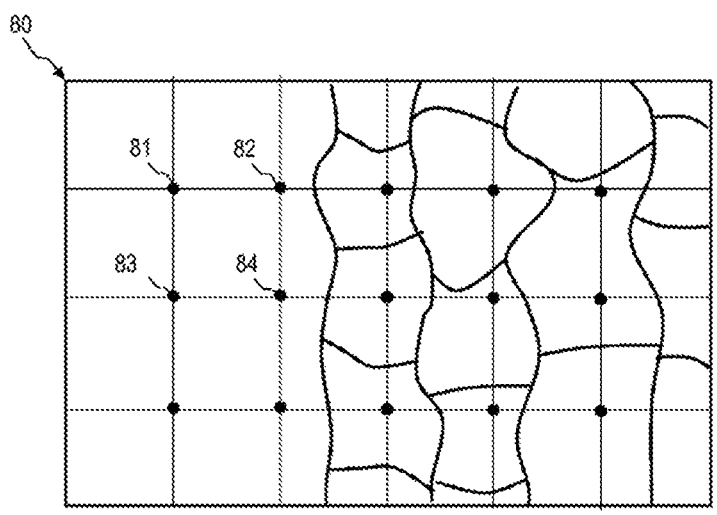
FIG. 7 illustrates the spatially resolved recording of Raman spectra according to one exemplary embodiment.

FIG. 7 shows a recording of Raman spectra at a plurality of regions 80. At the plurality of regions 80, which are depicted as points or solid circles 81-84, at least one Raman spectrum can be recorded in each case. To improve the statistics, it is also possible to record multiple Raman spectra at each of the points. Signal recording and relative movement between a slide and optical components of the Raman spectroscopy system can be automatically controlled by the evaluation unit 20. For example, it is possible at multiple separate small regions 81-84 to record Raman spectra in each case.

Although FIG. 7 schematically depicts a regular arrangement of points at which the Raman spectra are recorded, the recording can also be done at an irregular arrangement of points. It is possible to define different patterns of points at which the Raman spectroscopy is to be carried out in each case. At least some of the points 81-84 can be definable in a user-defined manner. The evaluation unit 20 can comprise an appropriate input interface which allows a user-defined definition of those points at which a Raman spectrum is to be recorded in each case.

The spatially resolved recording of the Raman spectra can be done at relatively large distances. According to exemplary embodiments, the spatially resolved recording of at least two Raman spectra can, however, also be done on subcellular structures. At least two Raman spectra can be recorded at different subcellular regions, for example for nuclei and cytoplasm, in the material 9 and evaluated by the evaluation unit 20.

By recording the Raman spectra at multiple regions 81-84 of the sample, it is possible to quantitatively ascertain the number of cells of one or more cell types. For example, it is possible to count the keratinocytes, melanocytes and/or fibroblasts which are present per area.

Figure 8:
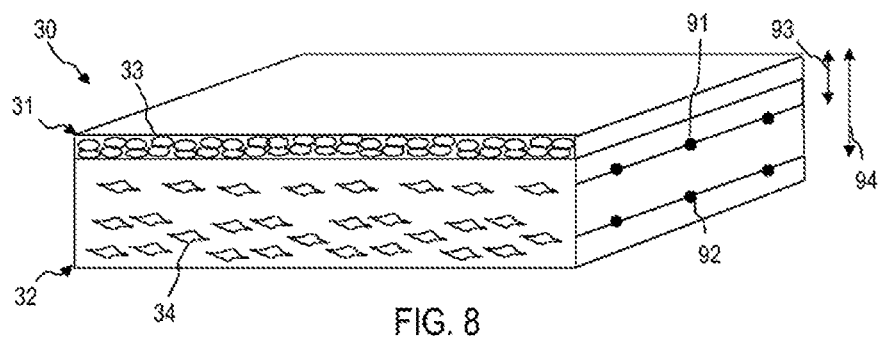
FIG. 8 illustrates the spatially resolved recording of Raman spectra according to one exemplary embodiment.

FIG. 8 illustrates points 91, 92 at which the signal recording by Raman spectroscopy can be done. The signal recording by the Raman spectroscopy allows the checking of the material 9 in different depths 93, 94 of the material 9 without having to destroy the material 9 for this purpose. The points 91, 92 at which a Raman spectrum or multiple Raman spectra is/are recorded in each case can define a regular or irregular lattice and can be arranged at different distances 93, 94 from the surface of the material 9.

Different cell types can still be reliably identified even in different depths using the Raman spectroscopy system of the device 1.

Figure 9:
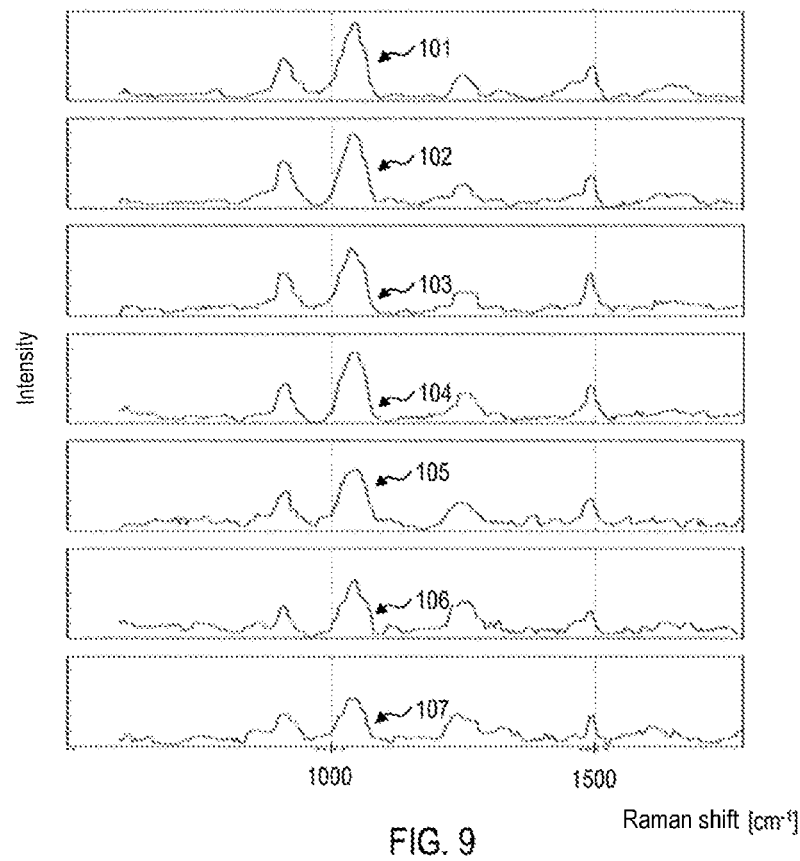
FIG. 9 illustrates Raman spectra recorded in different depths of the material.

FIG. 9 shows Raman spectra 101 to 107 which were recorded at depths different depths on a material 9 composed of fibroblasts. The Raman spectrum 101 was recorded on the surface of a material 9 consisting of fibroblasts. The Raman spectrum 102 was recorded at a depth of 40 μm from the surface of the material 9. The Raman spectrum 103 was recorded at a depth of 130 μm from the surface of the material 9. The Raman spectrum 104 was recorded at a depth of 170 μm from the surface of the material 9. The Raman spectrum 105 was recorded at a depth of 200 μm from the surface of the material 9. The Raman spectrum 106 was recorded at a depth of 220 μm from the surface of the material 9. The Raman spectrum 107 was recorded at a depth of 260 μm from the surface of the material 9.

The characteristic structures of the Raman spectrum for fibroblasts can be reliably identified even in different depths 93, 94 of the material 9. The ascertainment of different cell populations, i.e., the ascertainment of the absolute or relative number of cells of different cell types using Raman spectroscopy, can be carried out not only at the surface, but also in a three-dimensional material 9.

Figure 10:
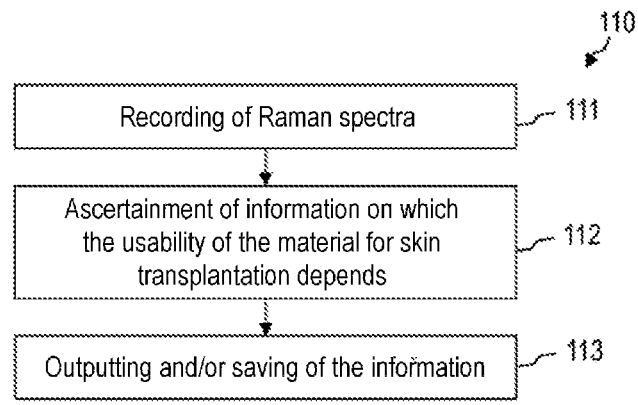
FIG. 10 is a flowchart of a method according to one exemplary embodiment.

FIG. 10 is a flowchart of a method 110 according to one exemplary embodiment. The method 110 can be carried out by the device 1.

In step 111, at least one Raman spectrum of the material 9 is recorded. The light source 11 is controlled such that an excitation beam 17 is generated. It is also possible to record multiple Raman spectra. For example, it is possible to record multiple Raman spectra at different positions of the same sample or on different samples in order to determine cell populations of different cell types.

In step 112, the evaluation unit 20 evaluates the recorded Raman spectrum. In this connection, the evaluation unit 20 can identify at least one Raman peak which is characteristic of one of multiple different cell populations of the material 9. The evaluation unit can identify at least one Raman peak which is characteristic of keratinocytes, melanocytes and/or fibroblasts. Alternatively or additionally, the evaluation unit 20 can identify at least one Raman peak which is characteristic of blood-vessel cells, hair-follicle cells, corneocytes, sebaceous-gland cells and sweat-gland cells. The evaluation unit 20 can carry out a cluster analysis on recorded Raman spectra in order to ascertain which cell types are present and/or in what relative number different cell types are present.

In step 113, it is optionally possible to save or output information relevant to the usability of the material 9 for the transplantation. For example, it is possible to specify information about the cell number and/or the relative number of different cell types.

Figure 11:
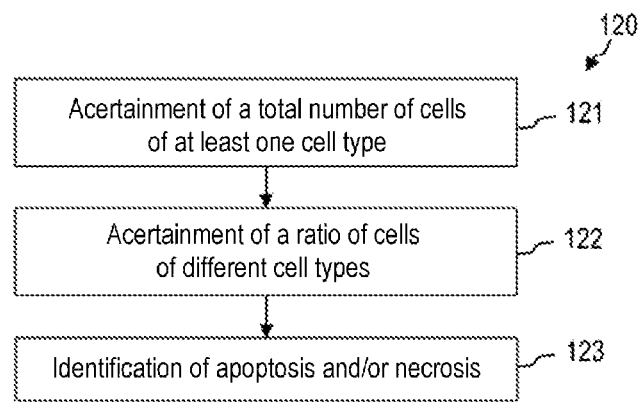
FIG. 11 is a flowchart of a method according to one exemplary embodiment.

FIG. 11 is a flowchart of a method 120 according to one exemplary embodiment. The method 120 can be carried out by the device 1. The method 120 can be used to ascertain information relating to the usability of the material 9 for the transplantation.

The method 120 can comprise the recording of at least one Raman spectrum, as has been elucidated for step 111.

In step 121, the evaluation unit 20 can evaluate the at least one recorded Raman spectrum in order to ascertain a total number of cells of a cell type or the total number of cells of different cell types in the material 9 or a subregion of the material 9. For example, it is possible to ascertain the number of fibroblasts, of keratinocytes and/or of melanocytes in a subvolume or a surface of the material 9 by evaluating the Raman spectrum. It is possible to record multiple Raman spectra in a spatially resolved manner in order to count cells of different cell types. For the counting, it is possible to evaluate spectral weights, intensities and/or the position of data points in a cluster analysis in order to ascertain the total number of cells of a cell type or the total number of cells of different cell types in the material 9 or a subregion of the material 9.

In step 122, the evaluation unit 20 can ascertain a ratio of a number of cells of a first cell type to cells of a second cell type. The evaluation unit can use spectral weights, intensities and/or the position of data points in a cluster analysis in order to obtain information about the relative size of different cell populations. The different cell populations can be selected from a group consisting of keratinocytes, melanocytes, fibroblasts, blood-vessel cells, hair-follicle cells, corneocytes, sebaceous-gland cells and sweat-gland cells.

In step 123, the evaluation unit 20 can optionally ascertain from the Raman spectra whether cells of one or more cell populations are subject to functional changes which reduce their suitability for the transplantation. For example, the evaluation unit 20 can ascertain whether cells of one or more cell populations, for example keratinocytes, melanocytes, fibroblasts, blood-vessel cells, hair-follicle cells, corneocytes, sebaceous-gland cells and/or sweat-gland cells, are impaired in terms of their function owing to apoptosis or necrosis.

An ascertainment of such a functional change can be identified in comparison with healthy, functioning cells, for example on the basis of a shift of the data points obtained in a principal component analysis or a different cluster analysis. On the basis of the proportion of data points beyond the regions 53, 54 for functioning cells, it is possible to ascertain whether keratinocytes, melanocytes, fibroblasts, blood-vessel cells, hair-follicle cells, corneocytes, sebaceous-gland cells and/or sweat-gland cells are subject to functional changes.

Figure 12:
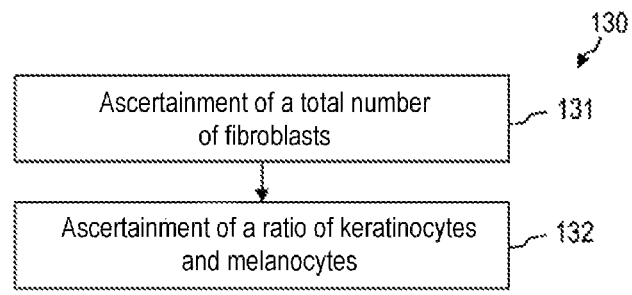
FIG. 12 is a flowchart of a method according to one exemplary embodiment.

FIG. 12 is a flowchart of a method 130 according to one exemplary embodiment. The method 130 can be carried out by the device 1. The method 130 can be used to ascertain information relating to the usability of the material 9 for the transplantation.

The method 130 can comprise the recording of at least one Raman spectrum, as has been elucidated for step 111.

In step 131, the evaluation unit 20 can evaluate the at least one recorded Raman spectrum in order to ascertain a total number of fibroblasts in the material 9 or a subregion of the material 9. To count the number of fibroblasts, it is possible to evaluate spectral weights, intensities and/or the position of data points in a cluster analysis in order to ascertain the total number of fibroblasts in the material 9 or a subregion of the material 9.

In step 132, the evaluation unit 20 can ascertain a ratio of a number of keratinocytes to a number of melanocytes. The evaluation unit can use spectral weights, intensities and/or the position of data points in a cluster analysis in order to obtain information about the relative size of the cell populations for keratinocytes and melanocytes.

Reference data used by the evaluation unit 20 for the evaluation of the Raman spectra recorded on the material 9 can be nonvolatilely saved in the memory 23. Alternatively or additionally, the device 1 can also be configured for machine-learning techniques in order to learn the criteria which make it possible to distinguish different cell types on the basis of Raman spectra, as will be described in more detail with reference to FIG. 13.

The checking of material for its suitability for the transplantation can be done in different method stages of a process for producing an autologous demo-epidermal skin substitute. The checking can be done sequentially multiple times.

For example, it is possible using devices and methods according to exemplary embodiments to check whether cells are suitable for cultivation in order to generate a skin substitute. To this end, the at least one Raman spectrum can be recorded on cells before they are introduced into or applied to a support material, for example a matrix. In this way, it is, for example, possible to identify different cell types, to quantitatively record relative proportions of different cell types and/or to identify functional impairments of one or more cell types. To this end, it is, for example, possible to compare the recorded Raman spectrum with one or more reference spectra. It is possible to use analysis techniques such as a cluster analysis in order to identify different cell types, to quantitatively record relative proportions of different cell types and/or to identify functional impairments of one or more cell types.

Alternatively or additionally, it is possible using devices and methods according to exemplary embodiments to check whether a support material, for example a matrix, is suitable for producing a skin substitute. To this end, the at least one Raman spectrum can be recorded on the matrix before skin cells are introduced into or applied to said matrix. In this way, it is, for example, possible to identify whether the material of the matrix corresponds to a desired material, for example collagen, and/or to identify contaminations. To this end, it is, for example, possible to compare the recorded Raman spectrum with one or more reference spectra. It is possible to use analysis techniques such as a cluster analysis in order to identify the material of the matrix, to identify the density of the matrix and/or to qualitatively and/or quantitatively record contaminations.

Alternatively or additionally, it is possible using devices and methods according to exemplary embodiments to check whether a skin substitute cultured from cells introduced into or applied to a support material, for example a matrix, is suitable for the transplantation. To this end, different cell types can be identified. It is possible to quantitatively evaluate the proportions of different cell types. It is possible to identify functional impairments of cells of one or more different cell types. To this end, the recorded at least one Raman spectrum can be compared with one or more reference spectra. Alternatively or additionally, it is possible to use analysis techniques such as a cluster analysis. Alternatively or additionally, it is possible to determine contaminations in the cell populations by foreign cells in the cultured tissue by means of evaluation of the Raman spectra.

Figure 13:
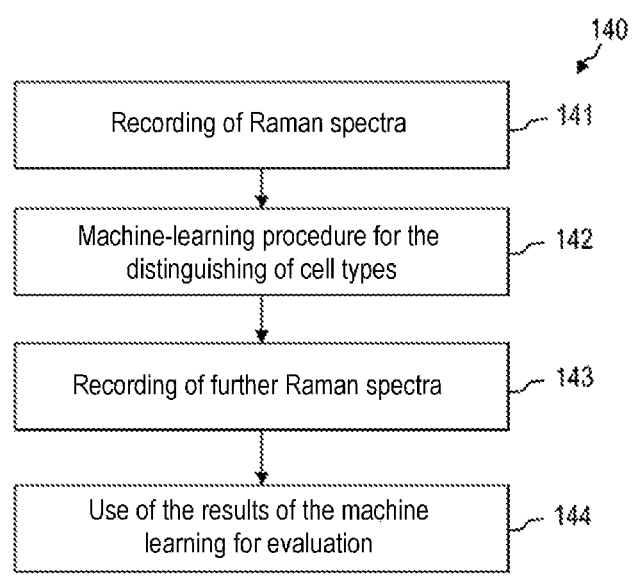
FIG. 13 is a flowchart of a method according to one exemplary embodiment.

FIG. 13 is a flowchart of a method 140 according to one exemplary embodiment. The method 140 can be carried out by the device 1. The method 140 can be used to ascertain information relating to the usability of the material 9 for the transplantation. Rules forming the basis of the assessment of the usability of the material 9 can be automatically learnt by the device 1 using a machine-learning method, especially by means of supervised learning. The rules can be nonvolatilely saved in the memory 23.

In step 141, multiple Raman spectra are recorded. The multiple Raman spectra can be recorded on keratinocytes, melanocytes, fibroblasts, blood-vessel cells, hair-follicle cells, corneocytes, sebaceous-gland cells and/or sweat-gland cells. The multiple Raman spectra can be recorded on an autologous demo-epidermal skin substitute for one or more patients.

In step 142, a machine-learning procedure can be carried out. The procedure can be one of supervised learning. In this connection, the device 1 can receive a user input for different recorded Raman spectra. The user input can, for example, assign Raman spectra, Raman peaks and/or clusters of a cluster analysis to different cellular constituents.

On the basis of the user input, the device 1 can set one or more parameters of a set of rules, on the basis of which the device 1 evaluates Raman spectra in order to assess the suitability of the material 9 for use as transplant. On the basis of the user input, the evaluation unit 20 can, for example, adjust one or more parameters of a support vector machine, by means of which recorded Raman spectra are evaluated in order to ascertain information about the suitability of the material 9 for use as transplant.

The learnt rules, for example the parameters of the support vector machine, can be saved by the device 1 in the memory 23.

In step 143, Raman spectra can be recorded on a material 9 to be checked.

In step 144, the saved rules can be applied to the recorded Raman spectra. This can, for example, be done as described with reference to FIG. 11 or FIG. 12. On the basis of the rules, it is possible to ascertain from the recorded Raman spectra which cell types are present in the material 9. On the basis of the rules, it is possible to ascertain from the recorded Raman spectra in what relative number cells of different cell types are present in the material 9. On the basis of the rules, it is possible to ascertain from the recorded Raman spectra whether cells of one or more cell types in the material 9 are subject to functional changes in comparison with fully functioning cells.

The devices and methods according to exemplary embodiments can be used not only for examining skin transplants, but also for examining other tissues, for example cartilage tissue and/or bone tissue, for their suitability for transplantation.

The evaluation unit of a device according to exemplary embodiments can be configured to identify chondrocytes, chondroclasts and/or chondroblasts. The evaluation unit of a device according to one exemplary embodiment can be configured to determine a number or density of chondrocytes, chondroclasts and/or chondroblasts in a spatially resolved manner in order to examine the suitability of a material as cartilage-tissue transplant.

The evaluation unit of a device according to exemplary embodiments can be configured to identify phenotypic changes of at least one cell selected from the group consisting of chondrocytes, chondroclasts and chondroblasts, by means of evaluation of the at least one Raman spectrum.

Figure 14:
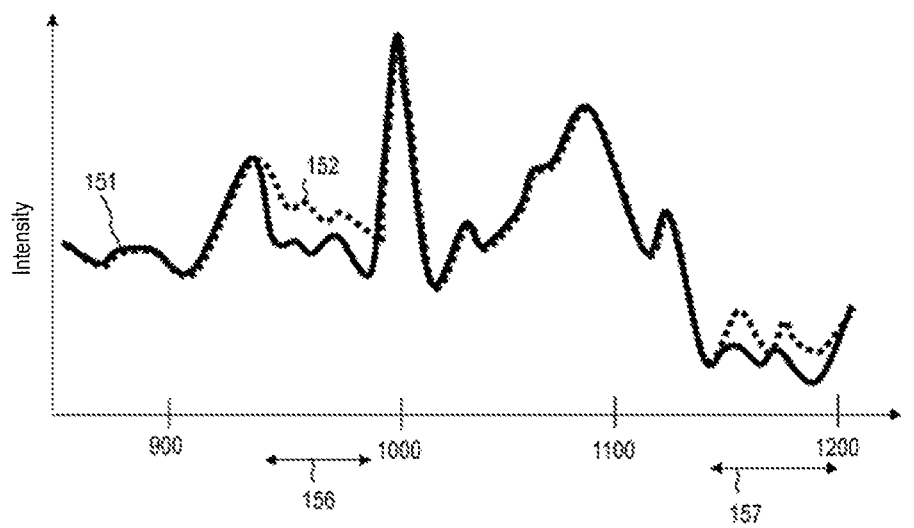
FIG. 14 shows exemplary Raman spectra which are recorded and evaluated by a device according to one exemplary embodiment.

FIG. 14 shows Raman spectra of fresh chondrocytes and of chondrocytes after in vitro cultivation. What is depicted by way of example is a portion of a Raman spectrum 151 of fresh chondrocytes and of a Raman spectrum 152 of chondrocytes after multiday in vitro cultivation.

The Raman spectrum 151 of fresh chondrocytes and the Raman spectrum 152 of chondrocytes after multiday in vitro cultivation differ in the position and/or the spectral weight of different Raman peaks. These differences can be used by the device 1 for the automatic distinguishing of fresh chondrocytes and chondrocytes after multiday in vitro cultivation.

Different wavenumbers or wavenumber intervals can be evaluated in order to examine chondrocytes for their suitability for use as transplant. For example, the Raman spectrum 151 of fresh chondrocytes have a different spectral weight in one or more spectral regions 156, 157 than the Raman spectrum 152 of chondrocytes after multiday in vitro cultivation. The wavenumber intervals 156, 157 can comprise one or more intervals, for example a wavenumber interval of from 900 $cm^{-1}$ to 1000 $cm^{-1}$, a wavenumber interval of from 950 $cm^{-1}$ to 1000 $cm^{-1}$, a wavenumber interval of from 1100 $cm^{-1}$ to 1200 $cm^{-1}$ or a wavenumber interval of from 1150 $cm^{-1}$ to 1200 $cm^{-1}$. An analysis of the Raman spectrum in one or more of the wavenumber intervals 156, 157 makes it possible to decide whether the cultivated chondrocytes are suitable for use as transplant.

It is not only the position and intensity of Raman peaks of a Raman spectrum which can be evaluated in order to examine cells or another material for the suitability for use as cartilage transplant. The device 1 can use the ratio of the intensities measured at two different Raman peaks in order to examine cells or another material for the suitability for use as cartilage transplant.

It is possible, though not absolutely necessary, to compare the Raman spectrum recorded on the material or multiple Raman spectra recorded on the material with information about reference spectra of chondrocytes, chondroclasts and/or chondroblasts. The Raman spectrum or the Raman spectra can be further processed by the evaluation unit 22 in order to distinguish different cell types. The evaluation unit 20 can, for example, carry out a cluster analysis, for example a principal component analysis of the recorded Raman spectrum. The result of the cluster analysis can be used in order to distinguish chondrocytes, chondroclasts and chondroblasts. The result of the cluster analysis can also be used in order to identify phenotypic changes in chondrocytes, chondroclasts and chondroblasts.

Figure 15:
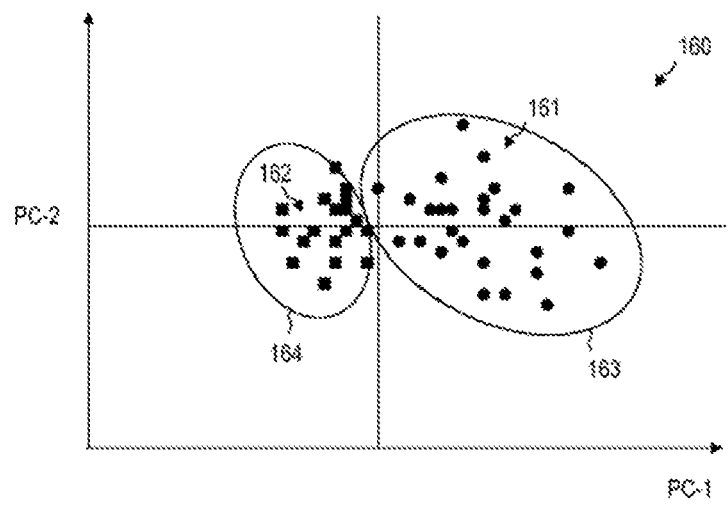
FIG. 15 illustrates processing of recorded Raman spectra by a device according to one exemplary embodiment.

FIG. 15 illustrates exemplary results of a cluster analysis carried out by the evaluation unit 20 in order to identify phenotypic changes in chondrocytes. What is carried out is the principal component analysis for a Raman spectrum or multiple Raman spectra which were recorded on the material. The data points are depicted in accordance with a pair of the different principal components PC-1 and PC-2. FIG. 15 shows the data points 161, which are assigned to fresh chondrocytes, and data points 162, which are assigned to chondrocytes with phenotypic changes.

The result of the cluster analysis of the Raman spectrum recorded on the material can be evaluated as to whether and how many data points lie in different regions 163, 164 of the coordinate system spanned by multiple principal components. For example, it is possible to ascertain how many data points lie in a region 163 assigned to fresh chondrocytes. It is possible to ascertain how many data points lie in a region 164 assigned to chondrocytes with phenotypic changes. It is possible to ascertain how many data points lie in further regions of the coordinate system spanned by multiple principal components, which regions are assigned to other cellular constituents of the material 9, for example chondroclasts and/or chondroblasts.

As is discernible from FIG. 15, the data points obtained by the principal component analysis shift depending on whether the material comprises fresh chondrocytes or chondrocytes changed phenotypically in comparison therewith. Accordingly, the evaluation unit 20 can, on the basis of the principal component analysis of a Raman spectrum or multiple Raman spectra, automatically determine which cell types are present and/or what proportion of the cells are subject to changes.

Raman spectroscopy can likewise be used in order to discover disease-induced changes in cartilage cells in order to assess the usability as transplant.

Figure 16:
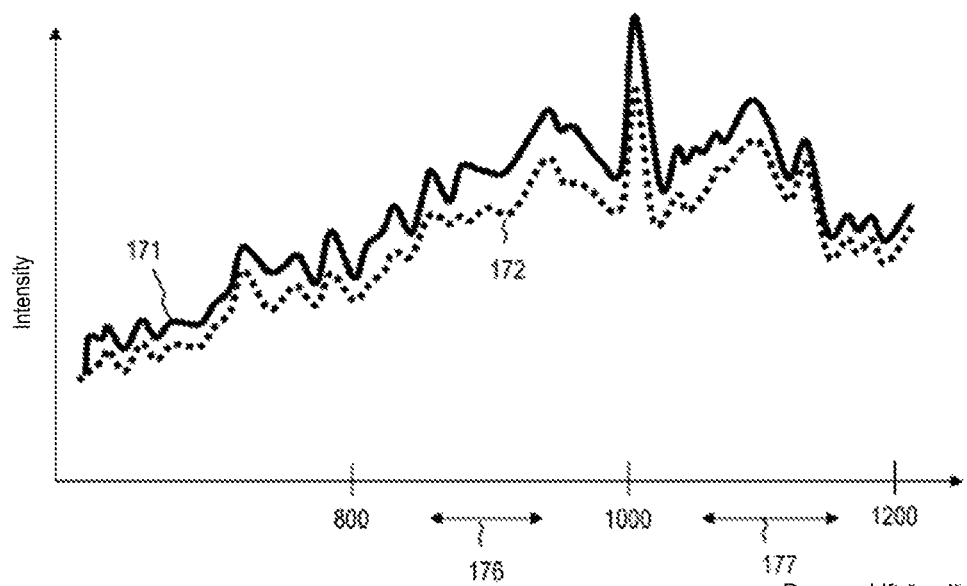
FIG. 16 shows exemplary Raman spectra which are recorded and evaluated by a device according to one exemplary embodiment.

FIG. 16 shows a portion of a Raman spectrum 171 of primary chondrocytes and a portion of a Raman spectrum 172 of cells derived from human chondrosarcoma cells (SW1353).

The Raman spectrum 171 of primary chondrocytes and the Raman spectrum 72 of cells derived from human chondrosarcoma cells (SW1353) differ in the intensity of different Raman peaks. These differences can be used by the device 1 for the automatic distinguishing of, for example, disease-induced changes.

Different wavenumbers or wavenumber intervals can be evaluated in order to examine chondrocytes for their suitability for use as transplant. For example, the Raman spectrum 171 of chondrocytes suitable for transplantation can have a different intensity in one or more spectral regions 176, 177 than the Raman spectrum 172 of cells subject to disease-induced changes. The wavenumber intervals 176, 177 can comprise one or more intervals, for example a wavenumber interval of from 800 $cm^{-1}$ to 1000 $cm^{-1}$, a wavenumber interval of from 850 $cm^{-1}$ to 950 $cm^{-1}$, a wavenumber interval of from 1000 $cm^{-1}$ to 1200 $cm^{-1}$ or a wavenumber interval of from 1050 $cm^{-1}$ to 11 500 $cm^{-1}$. An analysis of the Raman spectrum in one or more of the wavenumber intervals 176, 177 makes it possible to decide whether the cultivated chondrocytes are suitable for use as transplant.

It is possible, though not absolutely necessary, to compare the Raman spectrum recorded on the material or multiple Raman spectra recorded on the material with information about reference spectra of healthy chondrocytes, chondroclasts and/or chondroblasts. The Raman spectrum or the Raman spectra can be further processed by the evaluation unit 22 in order to distinguish healthy cells from diseased cells. The evaluation unit 20 can, for example, carry out a cluster analysis, for example a principal component analysis of the recorded Raman spectrum. The result of the cluster analysis can be used in order to assess whether chondrocytes, chondroclasts and chondroblasts are subject to disease-related changes.

Figure 17:
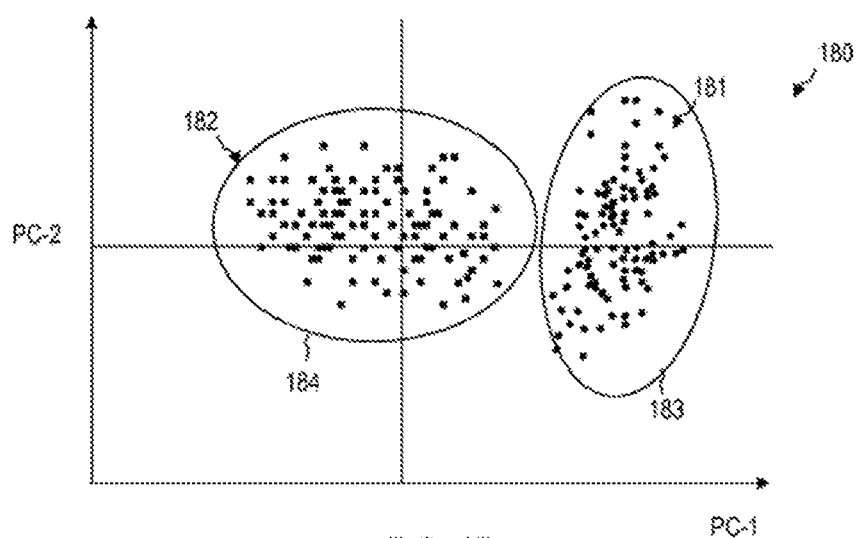
FIG. 17 illustrates processing of recorded Raman spectra by a device according to one exemplary embodiment.

FIG. 17 illustrates exemplary results of a cluster analysis carried out by the evaluation unit 20 in order to identify disease-related changes in chondrocytes. What is carried out is the principal component analysis for a Raman spectrum or multiple Raman spectra which were recorded on the material. The data points are depicted in accordance with a pair of the different principal components PC-1 and PC-2. FIG. 17 shows the data points 181, which are assigned to chondrocytes suitable for transplantation, and data points 182, which are assigned to chondrocytes changed due to disease.

The result of the cluster analysis of the Raman spectrum recorded on the material can be evaluated as to whether and how many data points lie in different regions 183, 184 of the coordinate system spanned by multiple principal components. For example, it is possible to ascertain how many data points lie in a region 183 assigned to chondrocytes suitable for transplantation. It is possible to ascertain how many data points lie in a region 184 assigned to chondrocytes changed due to disease. It is possible to ascertain how many data points lie in further regions of the coordinate system spanned by multiple principal components, which regions are assigned to other cellular constituents of the material 9, for example chondroclasts and/or chondroblasts.

As is discernible from FIG. 17, the data points obtained by the principal component analysis shift depending on whether the material comprises fresh chondrocytes or chondrocytes changed due to disease. Accordingly, the evaluation unit 20 can, on the basis of the principal component analysis of a Raman spectrum or multiple Raman spectra, automatically determine which cell types are present and/or what proportion of the cells are subject to disease-related changes.

Alternatively or additionally, the evaluation unit of a device according to exemplary embodiments can be configured to identify osteocytes, osteoclasts and/or osteoblasts. The evaluation unit of a device according to one exemplary embodiment can be configured to determine a number or density of osteocytes, osteoclasts and/or osteoblasts in a spatially resolved manner in order to examine the suitability of a material as bone transplant.

The evaluation unit of a device according to exemplary embodiments can be configured to examine, on the basis of the intensity and/or position of Raman peaks, whether bone tissue is suitable for transplantation. The evaluation unit of a device according to exemplary embodiments can be configured to examine, on the basis of the intensity and/or position of Raman peaks for chemical groups in mineral phases and collagen phases, whether bone tissue is suitable for transplantation. For example, the mineralization can be quantitatively determined.

Figure 18:
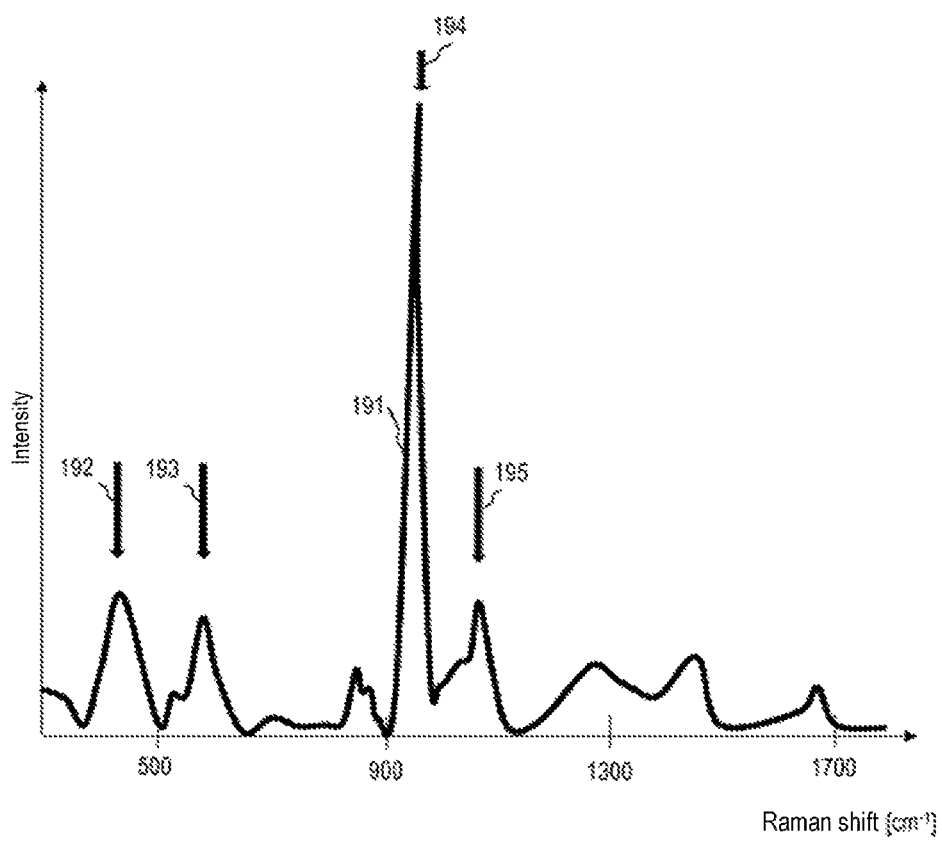
FIG. 18 shows an exemplary Raman spectra which is recorded and evaluated by a device according to one exemplary embodiment.

FIG. 18 shows a portion of a Raman spectrum 191 of bone tissue. The Raman spectrum 191 has Raman peaks which can be assigned to mineral phases and collagen phases.

For example, it is possible to identify, by means of evaluation of the Raman spectrum 191, a Raman peak 192 which can be assigned to $v_2$ phosphate mineral. Alternatively or additionally, the evaluation unit can be configured to identify, by means of evaluation of the Raman spectrum 191, a Raman peak 193 which can be assigned to $v_4$ phosphate mineral. Alternatively or additionally, the evaluation unit can be configured to identify, by means of evaluation of the Raman spectrum 191, a Raman peak 194 which can be assigned to $v_1$ phosphate mineral. Alternatively or additionally, the evaluation unit can be configured to identify, by means of evaluation of the Raman spectrum 191, one or more Raman peaks which can be assigned to collagen (e.g., amide III collagen, amide I collagen, proline-ring collagen).

On the basis of the relative intensities of one or more of these Raman peaks, it is possible to ascertain a relative ratio of cells selected from the group consisting of osteocytes, osteoclasts and osteoblasts. On the basis of the relative intensities of one or more of these Raman peaks, it is also possible to identify disease-related changes in osteocytes, osteoclasts and/or osteoblasts.

The devices and methods according to exemplary embodiments can repeat the recording and evaluation of the Raman spectra. In this way, it is, for example, possible to ascertain whether cultured tissue has not yet reached a state in which it is usable as transplant or whether the cultured tissue has already exceeded a state in which it is usable as transplant.

The devices and methods according to exemplary embodiments can be used for checking a multiplicity of different types of cultured tissue. For example, the devices and methods according to exemplary embodiments can be used to ascertain information relevant to the usability of cultured cartilage, cultured esophageal tissue, cultured intestinal tissue or cultured gastric tissue as transplant.

Devices and methods according to exemplary embodiments can be generally used for the quantitative examination of material in order to ascertain information relevant to the usability of the material 9 for the transplantation. The devices and methods can be used in particular for examining cultured transplants before they are transplanted to the patient. Skin transplants are one application area; however, the devices and methods are not restricted thereto.

The invention claimed is:

1. A device for checking a material for transplantation, comprising
a Raman spectroscopy system comprising a light source and focusing optical elements for carrying out Raman spectroscopy in a non-destructive manner on the material in order to record at least one Raman spectrum, and
an electronic evaluation unit configured to determine, depending on an evaluation of the at least one Raman spectrum, an item of information on which a suitability of the material for use in the transplantation depends,
wherein the Raman spectroscopy system is configured to automatically perform Raman measurements in a pre-selectable manner or pattern to record multiple Raman spectra in multiple depths of the material from 40 μm to 300 μm via movement of at least one of the light source and the focusing optical elements relative to the material in a depth direction of the material and in a plane orthogonal to the depth direction of the material, and
wherein the electronic evaluation unit is configured to determine the composition of the material for each of the multiple depths.

2. The device as claimed in claim 1, wherein the electronic evaluation unit is configured to identify at least one of a quality and suitability of the material for transplantation, by evaluation of the at least one Raman spectrum, at least one cell population of the material, which population is selected from the group consisting of: keratinocytes, melanocytes, fibroblasts, blood-vessel cells, hair-follicle cells, corneocytes, sebaceous-gland cells and sweat-gland cells, or a group consisting of chondrocytes, chondroclasts, and chondroblasts, or a group consisting of osteocytes, osteoclasts and osteoblasts.

3. The device as claimed in claim 2, wherein the electronic evaluation unit is configured to identify, by evaluation of the at least one Raman spectrum, at least two different cell populations of the material, of which each is selected from the group consisting of: keratinocytes, melanocytes, fibroblasts, blood-vessel cells, hair-follicle cells, corneocytes, sebaceous-gland cells and sweat-gland cells, or a group consisting of chondrocytes, chondroclasts, chondroblasts, or a group consisting of osteocytes, osteoclasts and osteoblasts.

4. The device as claimed in claim 2, wherein the electronic evaluation unit is configured to determine a composition of the material in at least one region of the material.

5. The device as claimed in claim 1, wherein the electronic evaluation unit is configured to determine from cell densities measured at different depths, by way of calculation, a total number or total density of cells of at least one cell type.

6. The device as claimed in claim 1, wherein the electronic evaluation unit is configured to carry out a cluster analysis of the at least one Raman spectrum.

7. The device as claimed in claim 6, wherein the electronic evaluation unit is configured to determine, depending on the cluster analysis, what proportion of keratinocytes, melanocytes, fibroblasts and/or endothelial cells is present in at least one region of the skin transplant; what proportion of chondrocytes, chondroclasts, and/or chondroblasts is present in at least one region of the cartilage transplant or what proportion of osteocytes, osteoclasts and/or osteoblasts is present in at least one region of the bone transplant.

8. The device as claimed in claim 1, wherein the electronic evaluation unit is configured to use a machine-learning method in order to assign a Raman spectrum of the multiple Raman spectra to a cell type in each case.

9. The device as claimed in claim 8, wherein the electronic evaluation unit is configured to use a supervised-learning method in order to assign a Raman spectrum of the at least one Raman spectrum to a cell type in each case.

10. The device as claimed in claim 1, wherein the electronic evaluation unit is configured to determine, depending on the evaluation of the at least one Raman spectrum, a total number of cells in the material.

11. The device as claimed in claim 1, wherein the electronic evaluation unit is configured to identify, depending on the evaluation of the at least one Raman spectrum, functional changes of at least one cell population of the material.

12. The device as claimed in claim 11, wherein the functional changes include at least one of an apoptosis and necrosis.

13. The device as claimed in claim 1, wherein the material comprises a cultured tissue for a transplant.

14. The device as claimed in claim 13, wherein the electronic evaluation unit is configured to output an item of Yes/No information which indicates whether the cultured tissue is usable or not as transplant, after an evaluation of multiple Raman spectra, which evaluation was used to assess a support material of the cultured tissue and/or cells of the cultured tissue.

15. The device as claimed in claim 1, wherein the material comprises cartilage tissue.

16. The device as claimed in claim 1, wherein the material comprises bone tissue.

17. The device as claimed in claim 1, wherein the material is a skin transplant, a cartilage transplant, or a bone transplant.

18. A method for checking a material for transplantation, comprising recording at least one Raman spectrum of the material, and determining, by means of evaluation of the at least one Raman spectrum, an item of information on which a suitability of the material for use in the transplantation depends, wherein the method is carried out by a device for checking a material for transplantation, comprising a Raman spectroscopy system comprising focusing optical elements for carrying out Raman spectroscopy in a non-destructive manner on the material in order to record at least one Raman spectrum, and an electronic evaluation unit configured to determine, depending on an evaluation of the at least one Raman spectrum, an item of information on which a suitability of the material for use in the transplantation depends, wherein multiple Raman spectra are automatically performed in a pre-selectable manner or pattern in multiple depths of the material from 40 μm to 300 μm.

* * * * *